United States Patent
Truyens

(10) Patent No.: US 10,190,994 B2
(45) Date of Patent: Jan. 29, 2019

(54) APPARATUS, METHOD AND COMPUTER PROGRAM PRODUCT FOR INSPECTION OF AT LEAST SIDE FACES OF SEMICONDUCTOR DEVICES

(71) Applicant: KLA-Tencor Corporation, Milpitas, CA (US)

(72) Inventor: Carl Truyens, Rotselaar (BE)

(73) Assignee: KLA-Tencor Corporation, Milpitas, CA (US)

( * ) Notice: Subject to any disclaimer, the term of this patent is extended or adjusted under 35 U.S.C. 154(b) by 102 days.

(21) Appl. No.: 15/265,186

(22) Filed: Sep. 14, 2016

(65) Prior Publication Data

US 2017/0003231 A1 Jan. 5, 2017

Related U.S. Application Data

(63) Continuation of application No. PCT/US2015/042194, filed on Jul. 27, 2015.

(60) Provisional application No. 62/171,906, filed on Jun. 5, 2015.

(51) Int. Cl.
*G01N 21/95* (2006.01)
*H01L 21/66* (2006.01)
*G01N 21/88* (2006.01)

(52) U.S. Cl.
CPC ..... *G01N 21/9503* (2013.01); *G01N 21/8806* (2013.01); *H01L 22/12* (2013.01); *G01N 2201/0636* (2013.01)

(58) Field of Classification Search
CPC .................................................. G01N 21/9503
USPC .............................................. 356/237.2
See application file for complete search history.

(56) References Cited

U.S. PATENT DOCUMENTS

| | | | |
|---|---|---|---|
| 5,909,285 A | 6/1999 | Beaty et al. | |
| 6,094,263 A | 7/2000 | Tomiya et al. | |
| 6,339,337 B1 | 1/2002 | Matsuda et al. | |
| 2001/0048867 A1* | 12/2001 | Lebar | C23C 16/4583 414/217 |
| 2002/0135757 A1* | 9/2002 | Shires | G01N 21/88 356/237.1 |
| 2005/0084137 A1* | 4/2005 | Kim | G06K 9/00268 382/115 |

(Continued)

FOREIGN PATENT DOCUMENTS

| | | |
|---|---|---|
| CN | 2791639 | 6/2006 |
| EP | 2699071 | 2/2014 |
| JP | 2006140391 | 6/2006 |

*Primary Examiner* — Tarifur Chowdhury
*Assistant Examiner* — Omar Nixon
(74) *Attorney, Agent, or Firm* — Simpson & Simpson, PLLC

(57) ABSTRACT

An apparatus, a method and a computer program product for inspecting at least side faces of a semiconductor device are disclosed. A frame construction is provided, which holds a camera, defining an imaging beam path. The semiconductor device is inserted into a mirror block. The mirror block has a first mirror, a second mirror, a third mirror and a fourth mirror, wherein the mirrors are arranged such that they surround a free space in the form of a rectangle. The opposing first mirror and third mirror are fixedly mounted and the opposing second mirror and fourth mirror movably mounted. A tilted mirror directs an image of the side faces of the semiconductor substrate generated by the mirror block to the camera.

24 Claims, 9 Drawing Sheets

(56) References Cited

U.S. PATENT DOCUMENTS

| | | | |
|---|---|---|---|
| 2005/0185181 A1 | 8/2005 | Salvi | |
| 2006/0076675 A1* | 4/2006 | Hori | H01L 21/565 257/718 |
| 2006/0280493 A1* | 12/2006 | Kim | G03B 3/10 396/133 |
| 2009/0003815 A1* | 1/2009 | Polidor | G02B 7/32 396/106 |
| 2009/0041309 A1* | 2/2009 | Kim | G06K 9/00604 382/117 |
| 2010/0079883 A1* | 4/2010 | Englander | B60R 1/083 359/877 |
| 2015/0138341 A1 | 5/2015 | Amanullah | |

* cited by examiner

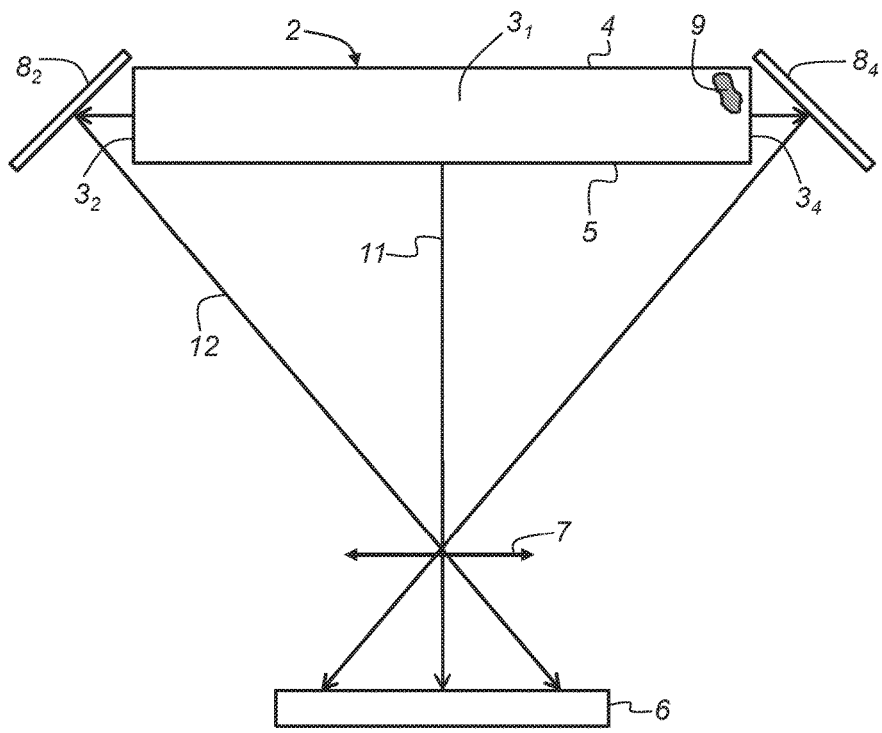
Prior Art      Fig. 1
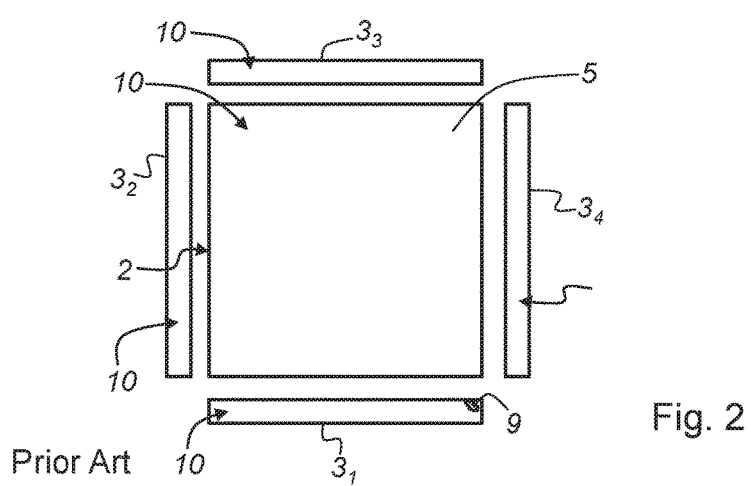
Prior Art      Fig. 2

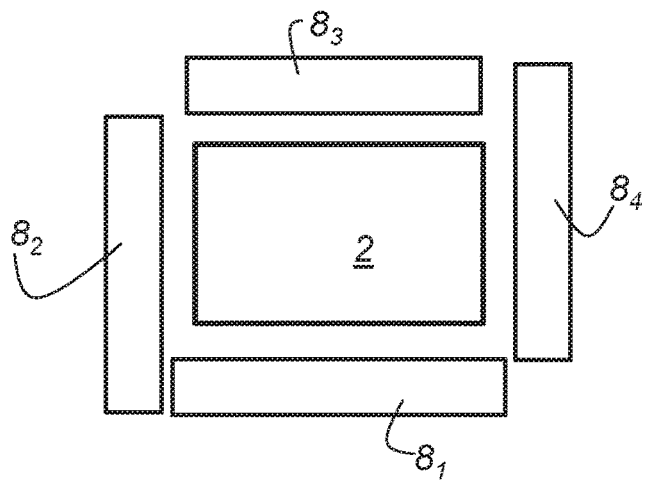
Fig. 3A
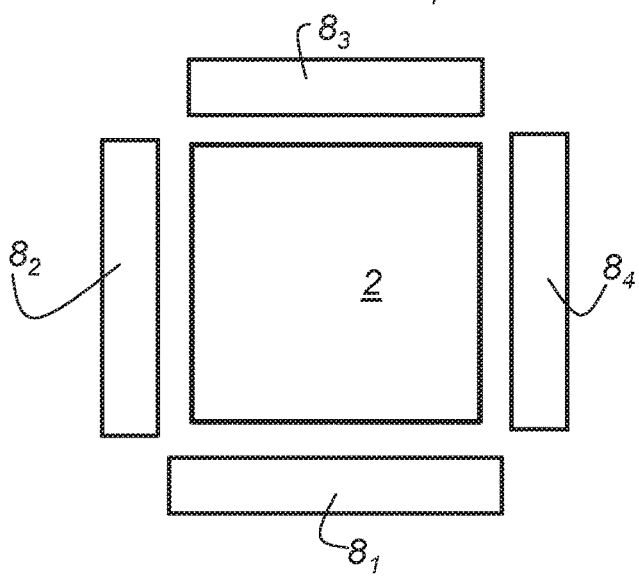
Fig. 3B
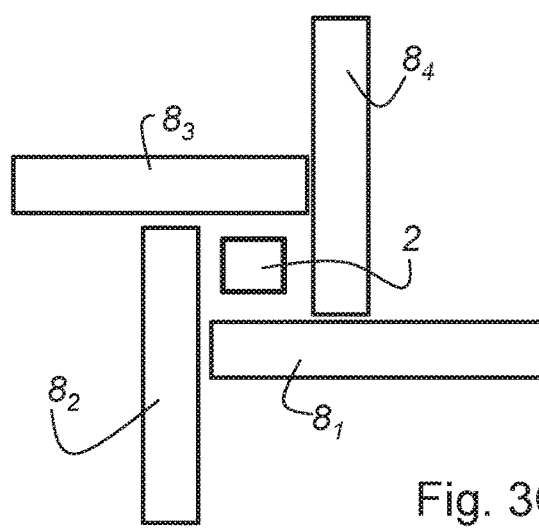
Prior Art    Fig. 3C

APPARATUS, METHOD AND COMPUTER PROGRAM PRODUCT FOR INSPECTION OF AT LEAST SIDE FACES OF SEMICONDUCTOR DEVICES

CROSS-REFERENCE TO RELATED APPLICATIONS

This application is filed under 35 U.S.C. § 120 and § 365(c) as a continuation of International Patent Application Serial No. PCT/US2015/042194, filed on Jul. 27, 2015, which application claims the benefit under 35 U.S.C. § 119(e) of U.S. Provisional Patent Application No. 62/171,906 filed on Jun. 5, 2015, which applications are incorporated herein by reference in their entireties.

TECHNICAL FIELD

The present invention refers to an apparatus for the inspection of at least side faces of a semiconductor device.

Furthermore, the present invention refers to a method for the inspection of at least side faces of a semiconductor device.

Additionally, the present invention refers to a computer program product disposed on a non-transitory computer readable medium for the inspection of at least side faces of a semiconductor device, the product comprising computer executable process steps operable to control a computer.

BACKGROUND

For example, U.S. Pat. No. 6,339,337 B1 discloses an infrared ray test for a semiconductor chip. The test is conducted by irradiating an infrared ray onto a bottom surface of a semiconductor chip, receiving the infrared ray reflected from a bonding pad and displaying the image of the bonding pad on a monitor. The image obtained from the infrared ray has information whether the bonding pad itself or a portion of the silicon substrate underlying the bonding pad has a defect or whether or not there is a deviation of the bonding pad with respect to the bump.

Chinese utility model CN 2791639 (Y) discloses a detecting device, which is mainly used for detecting internal defects of semiconductor material of which the band gap is larger than 1.12 eV. The detecting device for detecting internal defects of semiconductor material is composed of an optical microscope, an infrared CCD camera, video cable, a simulation image monitor, a digital image collection card, a computer and analysis process and display software.

Additionally, EP 2 699 071 A2 discloses an optoelectronic method for recording in heat diagram form the temperature distribution of land in which an infrared linescan system is used in an aircraft. The apparatus utilizes a rotary scanning mirror system receiving heat radiation through windows. The mirror system has four reflecting sides and is rotated about an axis by an electric motor. The radiation being directed by mirrors to an IR lens and thence to a row of optoelectronic receiver elements. The row of receiver elements is parallel to the axis of rotation of the mirror system, each receiver element being individually connected by a lead and an amplifying device to a corresponding one of a number of luminescent diodes.

The traditional method for finding side defects 9 in a semiconductor device 2 is shown in FIG. 1. A four sided or a five sided inspection is carried out. The semiconductor device 2 has a first side face 31, a second side face 32, a third side face 33, a fourth side face 34, a top face 4 and a bottom face 5. In the setup of FIG. 1 a camera 6 with a lens 7 looks to the bottom face 5 of the semiconductor device 2. A mirror 8 is arranged under 45 degrees with each of the first side face 31, the second side face 32, the third side face 33 and the fourth side face 34 of the semiconductor device 2, respectively. In FIG. 1 only the second mirror 82 arranged with respect to the second side face 32 and the fourth mirror 84 arranged with fourth side face 34 of the semiconductor device 2 are shown.

The setup of FIG. 1 is used obtain an image 10 (see FIG. 2) the first side face 31, the second side face 32, the third side face 33, the fourth side face 34 and the bottom face 5, respectively. The setup of FIG. 1 has significant drawbacks. The optical length 11 of the bottom face 5 view differs from the optical length 12 of the first side face 31 view, the second side face 32 view, the third side face 33 view and the fourth side face 34 view. Therefore, the focus is always a trade-off between focus on the bottom face 5 of the semiconductor device 2 and focus on the first side face 31, the second side face 32, the third side face 33 and the fourth side face 34, respectively. In case an image showing both the four side faces 31, 32, 33,34 and the bottom face 5 is to be obtained, in a process often called 5S inspection, the optical system needs a very large depth-of-focus, in order to keep both the four side faces 31, 32, 33,34 and the bottom face 5 in focus. This becomes very challenging when magnification increases.

According to a prior art method custom made mirror blocks are swapped. For a family of sizes of a semiconductor device, a custom mirror block (block with four 40-48 degree mirrors) is used. When another family of semiconductor devices needs to be inspected, the complete mirror block must be exchanged. The drawbacks are that one needs to keep expensive conversion parts and the lead time. Main disadvantages are: cost, flexibility, manual conversion, and risk of mistake. Conversion parts are needed for every family of semiconductor device sizes. These parts are custom so must be designed and manufactured when they are not yet available. This results in loss of flexibility as design must be started prior to having the family of semiconductor devices coming on-line. When the tool is converted, a line-technician or operator needs to manually change the mirror blocks. When the wrong type is mounted, damage to the tool or semiconductor device can result.

Another prior art solution is a motorization of the mirrors of the mirror block which is divided over two individual inspection stations: The front and rear images of the side faces of the semiconductor device are taken by one optical set-up that is automated. The left and right images of the side faces of the semiconductor device are taken by another optical set-up that is automated as well. So when the semiconductor device size changes, the mirrors are automatically adjusted on two inspection stations. The drawbacks are: the semiconductor devices need to pass by two inspection stations, two inspection stations increase costs and two inspection stations consume more space.

A further prior art method is that the unit or the mirror block is moved. In this concept the front/left side faces of the semiconductor device are inspected which is followed by a move of the unit or the mirror block, and then the rear/right side faces of the semiconductor device are inspected (other permutations are possible where always 2 adjacent sides are inspected). The major drawback is that the inspection is slow, which reduces throughput.

A motorization of all four mirrors 81, 82, 83 and 84 according to a prior art design is shown in FIGS. 3A to 3C. Here the set of the first mirror 81 and the third mirror 83, and the set and of the second mirror 82 and the fourth mirror 84 are moved and adapted to the size of the semiconductor device 2. The drawbacks of this arrangement are that it is very complicated and is only applicable for a limited range of sizes of the semiconductor devices.

SUMMARY

It is an object of the invention to provide an apparatus for inspecting at least side faces of a semiconductor device, which is cost effective, flexible, reliable, save and easy to use in a variety of applications.

The above object is achieved by an apparatus for inspecting at least side faces of a semiconductor device. The apparatus includes a camera, defining an imaging beam path, a mirror block, having a first mirror, a second mirror, a third mirror, and a fourth mirror, the mirrors being arranged such that they surround a free space in the form of a rectangle and that the opposing first mirror and third mirror are fixedly mounted and the opposing second mirror and fourth mirror are movably mounted, and a tilted mirror, for directing to an image of the side faces from the mirror block to the camera.

The advantage of the inventive apparatus is the flexibility. Once the inventive apparatus (inventive optical module) is installed, a whole range of semiconductor device sizes (square and rectangular) can be handled without the need of new parts. Optical resolution stays equal for the complete range of types of semiconductor devices. So no recalibration or resolution modeling is required. Additionally, the compactness of the inventive apparatus allows that the whole assembly can be mounted in a single slot of a turret based machine.

It is a further object of the invention to provide a method for inspecting at least side faces of a semiconductor device, wherein the method is easy to apply, works for a plurality of various types of semiconductor devices, is cost effective, flexible, reliable, save and easy to use in a variety of applications.

This object is achieved by a method for inspecting at least side faces of a semiconductor device, the method including placing the semiconductor device centrally into a free space defined by a mirror block, having a first fixed mirror and a third fixed mirror, and a second movable mirror and a fourth movable mirror, providing information about a type of the semiconductor device to a control unit, moving the second mirror and the fourth mirror such that a first distance between a respective side face of the semiconductor device and the second mirror and the fourth mirror, respectively, is equal to a second distance between a respective side face of the semiconductor device and the first fixed mirror and the third fixed mirror, respectively, and adjusting a focus position of the camera along an imaging beam path to compensate for a change in a focal distance.

The advantage of the inventive method is the flexibility because a whole range of semiconductor device sizes (square and rectangular) can be handled without the need to exchange parts for the ongoing inspection process. With the inventive method the semiconductor devices can be inspected in a reliable, fast and uncomplicated manner.

An object of the invention is as well to provide a computer program product disposed on a non-transitory computer readable medium for inspecting at least side faces of a semiconductor device which allows the inspection of a plurality of various types of semiconductor devices, is flexible to use and avoids damage of semiconductor devices under inspection.

The above object is achieved by a computer program product disposed on a non-transitory computer readable medium for inspection of at least side faces of a semiconductor device, the product including computer executable process steps operable to control a computer to place the semiconductor device with a placing mechanism into a free space of a mirror block; determine a type to the semiconductor device, move, according to the type to the semiconductor device, a second mirror and a fourth mirror of the mirror block such that a first distance between a respective side face of the semiconductor device and the second mirror and the fourth mirror is equal to a second distance between a respective side face of the semiconductor device and a first fixed mirror and a third fixed mirror of the mirror block, and adjusting a focus position of a camera along an imaging beam path in order to obtain a focused image of the at least four side faces of the semiconductor device.

Typical defects to be detected by the present invention are side cracks created by the dicing process of the semiconductor devices or embedded cracks created by internal stress in the work piece. In case the work piece is a semiconductor device, the internal stress can exist for example between the dielectric layer and the silicon structure. It is noted, that the invention (apparatus, method and computer program) is not restricted to semiconductor devices and is applicable for side and internal defects in general.

The main innovation of the apparatus is that two mirrors are fixed in combination with two symmetrically moving mirrors. When the semiconductor device is replaced with a semiconductor device of different size, the moving mirrors are repositioned, so that the distance between the side faces of the semiconductor device and the fixed mirrors equals the distance between the side daces of the semiconductor device and the moving mirrors. To compensate for the change in focal distance, the camera moves linearly. This could also be accomplished by using a zoom-lens set-up with auto-focus.

Due to the compactness of the inventive apparatus, which is an elongated module, the described invention is a key building block in a turret-based wafer-to-tape inspection machine. In this tool, a compact auto conversion optical set-up is needed.

According to an embodiment of the invention an apparatus for inspection of at least side faces of a semiconductor device has a housing, which defines a compact module. Inside the housing a camera, defining an imaging beam path, is linearly movable along the imaging beam path. The at least four side faces of the semiconductor device are imaged with a mirror block. The mirror block carries a first mirror, a second mirror, a third mirror and a fourth mirror. The mirrors are arranged such that they surround a free space in the form of a rectangle. The free space of the mirror block is accessible from the outside of the housing. The opposing first mirror and third mirror are fixedly mounted and the opposing second mirror and fourth mirror are movably mounted, which allows an adjustment of the inventive apparatus to the various types of semiconductor device. A tilted mirror is arranged in the housing with respect to the camera and the mirror block, such that an image of at least the side faces of the semiconductor device in the mirror block is directed to the camera.

A first motor, which is arranged in the housing, is used to move the camera in a linear motion in the direction of the image beam path. A second motor, which is arranged inside the housing, is assigned to the opposing second mirror and fourth mirror for positing them in such a way that a first distance between a side face of the semiconductor device and the respective first and third fixed mirrors equals a second distance between a side face of the semiconductor device and the respective second and fourth mirrors. The tilted mirror is arranged in the housing with respect to the camera and the mirror block such that an image of at least the side faces of the semiconductor device in the mirror block is directed to the camera. The moving mirrors in combination with zoom-lens/autofocus allow for an adjustment of the focus position, so that all types of semiconductor devices are imaged with the correct focus position.

With the invention swapping custom made mirror blocks is no longer necessary. For a family of sizes of a semiconductor device, a mirror block with two opposing movable mirrors is used. There is no longer the need to exchange the complete mirror block. This saves costs, since no expensive conversion parts are needed and the lead time is reduced.

Another embodiment relates to an apparatus including in the housing a light source for generating light in order to illuminate the side faces of the semiconductor device.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

Below, the invention and its advantages will be further described with reference to the accompanying figures in which:

FIG. 1 is a prior art set-up for detecting interior defects by looking at the sides of a semiconductor device;

FIG. 2 is a schematic representation of an image obtained by the set-up shown in FIG. 1;

FIG. 3A is a schematic representation of a traditional arrangement of four motorized mirrors in order to adapt to the various sizes of the semiconductor device;

FIG. 3B is a schematic representation of a traditional arrangement of four motorized mirrors in order to adapt to the various sizes of the semiconductor device;

FIG. 3C is a schematic representation of a traditional arrangement of four motorized mirrors in order to adapt to the various sizes of the semiconductor device;

DETAILED DESCRIPTION

Figure 4:
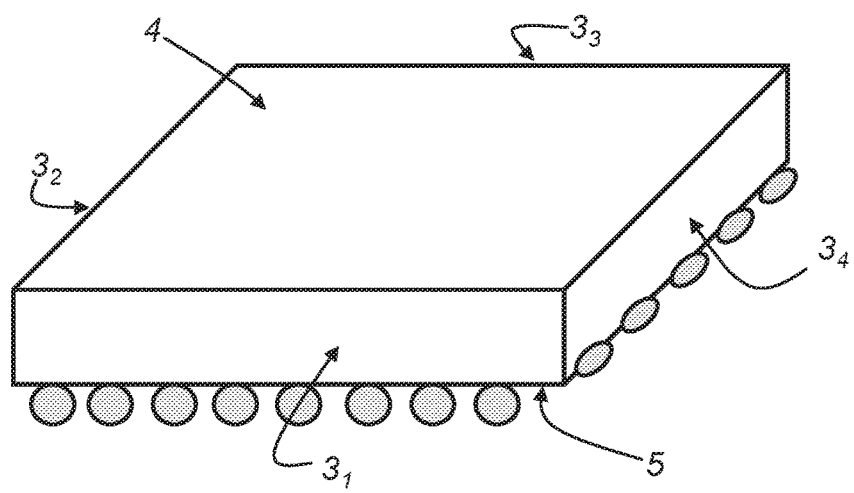
FIG. 4 is a schematic representation of a semiconductor device to be inspected.

In the figures like reference numerals are used for like elements or elements of like function. Furthermore, for the sake of clarity, only those reference numerals are shown in the figures which are necessary for discussing the respective figure.

FIG. 4 is a schematic representation of a semiconductor device 2 which is inspected by an apparatus or method of the present invention. The semiconductor device 2 has the form of a cuboid with a first side face 31, a second side face 32, a third side face 33, a fourth side face 34, a top face 4, and a bottom face 5. There are different types of semiconductor devices which differ in the outer dimensions.

Figure 5:
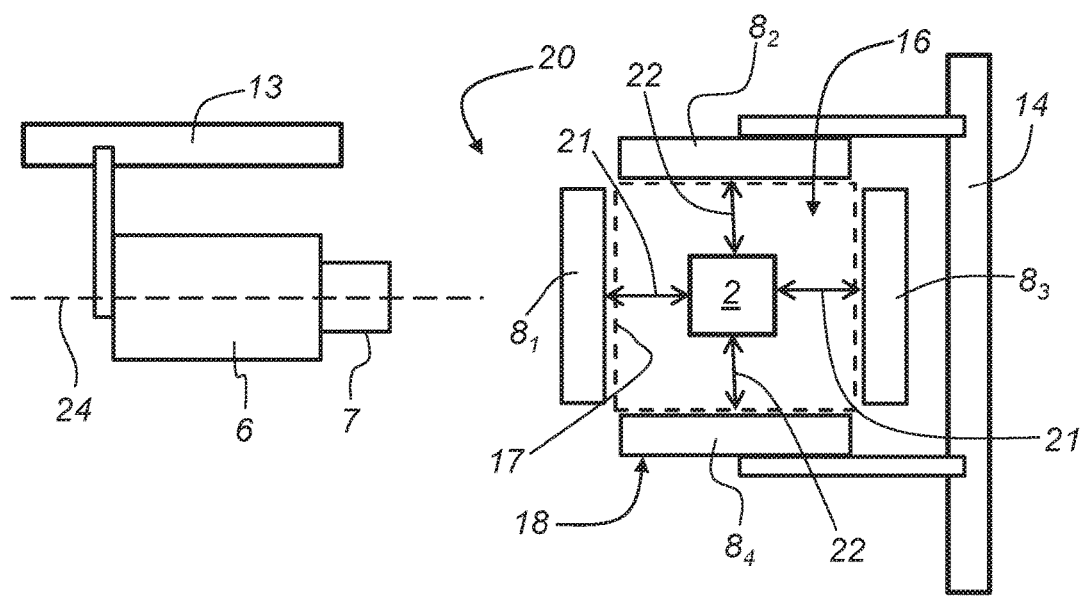
FIG. 5 is a schematic top view of the apparatus for carrying out the inspection of four side faces of a first type of a semiconductor device.

FIG. 5 is a schematic top view of the apparatus 20 for carrying out the inspection of the first side face 31, the second side face 32, the third side face 33, and the fourth side face 34 of a first type of the semiconductor device 2. According to the top view shown in FIG. 5, the various types of the semiconductor devices 2 can have the form of a rectangle or a square. A mirror block 18 defines a free space 16, into which the semiconductor device 2 to be inspected is positioned. The free space 16 of the mirror block 18 is defined by a first mirror 81, a second mirror 82, a third mirror 83, and a fourth mirror 84. The free space 16 has the form of a rectangle 17 (see dashed lines in FIG. 5). The first mirror 81, the second mirror 82, the third mirror 83, and the fourth mirror 84 are arranged parallel to the sides of the rectangle 17.

The opposing first mirror 81 and third mirror 83 are fixedly mounted. The opposing second mirror 82 and fourth mirror 84 are movably mounted. The second mirror 82 and the fourth mirror 84 are coupled with a second motor 14. With the second motor 14 a symmetric position change of the second mirror 82 and the fourth mirror 84 can be effected. By the position change a second distance 22 between second mirror 82 and a corresponding side face of the semiconductor device 2, as well as a second distance 22 between fourth mirror 84 and a corresponding side face of the semiconductor device 2 can be made equal to a first distance 21 between first mirror 81 and a corresponding side face of the semiconductor device 2, as well as equal to a first distance 21 between a third mirror 83 and a corresponding side face of the semiconductor device 2.

The camera 6 captures with its lens 7 an image of the four side faces 31, 32, 33 and 34 (see FIG. 4) of the semiconductor device 2. The camera 6 defines an imaging beam path 24 and can be moved linearly by a first motor 13 along the imaging beam path 24. The movement of the camera 6 is necessary to compensate for the change in focal distance of the apparatus 20. According to another embodiment of the invention, the linear movement of the camera 6 can be substituted by a zoom-lens set-up with auto-focus.

Figure 6:
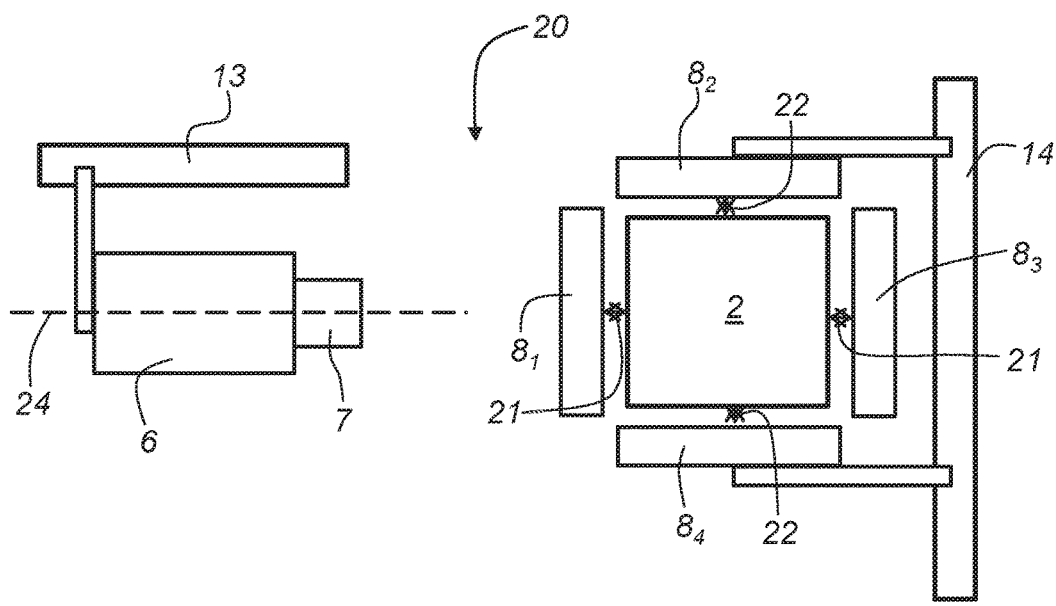
FIG. 6 is a schematic top view of the apparatus for carrying out the inspection of four side faces of a second type of a semiconductor device.
Figure 7:
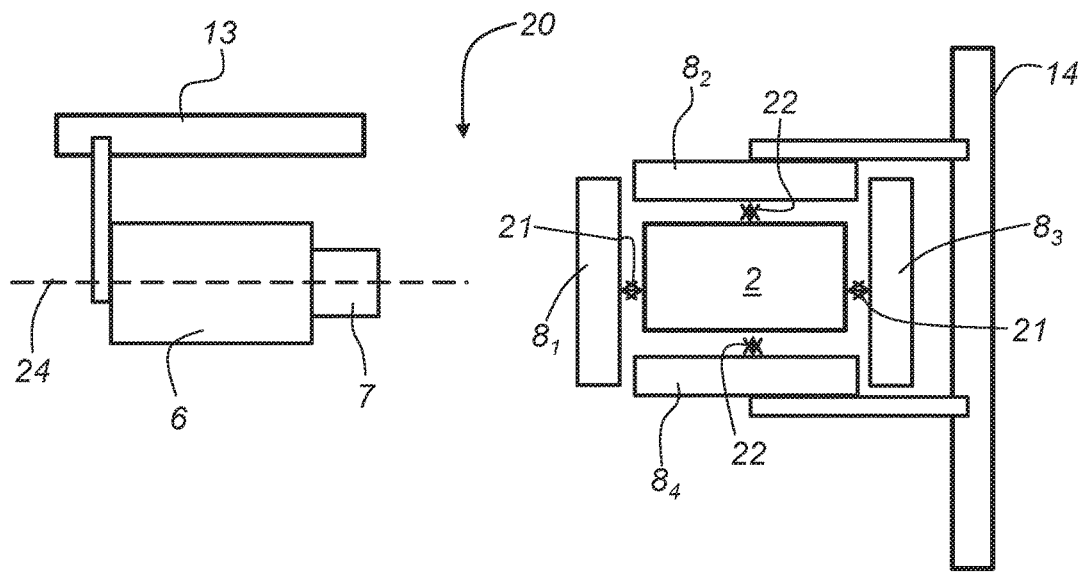
FIG. 7 is a schematic top view of the apparatus for carrying out the inspection of four side faces of a third type of a semiconductor device.
Figure 8:
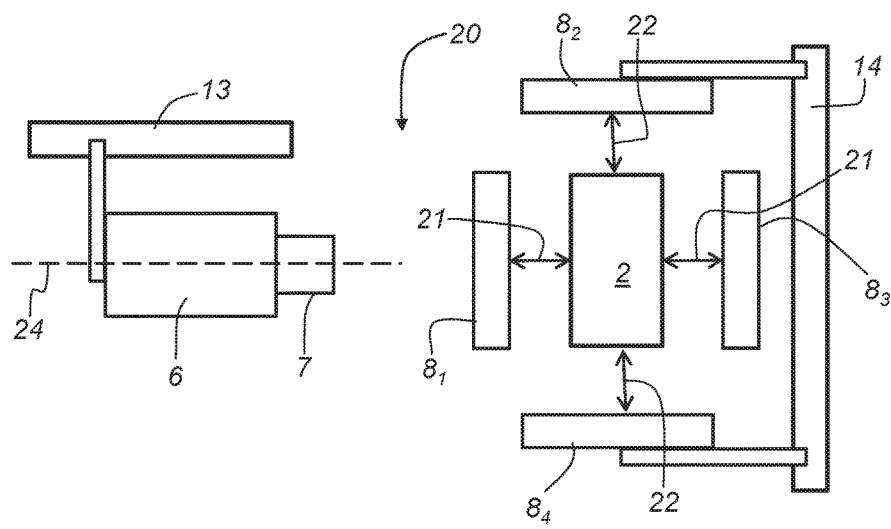
FIG. 8 is a schematic top view of the apparatus for carrying out the inspection of four side faces of a fourth type of a semiconductor device.

FIG. 6, FIG. 7 and FIG. 8 show the inventive apparatus 20 wherein different types of the semiconductor device 2 are inspected. Once the mirror block 18 is installed in the inventive apparatus 20, the apparatus 20 achieves full flexibility to inspect a whole range of sizes (square and rectangular) of semiconductor devices 2. The semiconductor devices 2 can be handled without the need for new parts.

FIG. 6 shows the situation that a large, square semiconductor device 2 is inspected. The second motor 14 carries out a symmetric position change of the second mirror 82 and the fourth mirror 84. By the position change a second distance 22 between second mirror 82 and a corresponding side face of the semiconductor device 2, as well as a second distance 22 between fourth mirror 84 and a corresponding side face of the semiconductor device 2 can be made equal to a first distance 21 between first mirror 81 and a corresponding side face of the semiconductor device 2, as well as equal to a first distance 21 between a third mirror 83 and a corresponding side face of the semiconductor device 2. The camera adjusts a focus position along the imaging beam path 24. According to a preferred embodiment the first motor 13 moves the camera 6 along the imaging beam path 24. The movement of the camera 6 is necessary to compensate for the change in focal distance of the apparatus 20.

FIG. 7 shows the situation that a rectangular semiconductor device 2 is inspected. The second motor 14 carries out a symmetric position change of the second mirror 82 and the fourth mirror 84. By the position change a second distance 22 between second mirror 82 and a corresponding side face of the semiconductor device 2, as well as a second distance 22 between fourth mirror 84 and a corresponding side face of the semiconductor device 2 can be made equal to a first distance 21 between first mirror 81 and a corresponding side face of the semiconductor device 2, as well as equal to a first distance 21 between a third mirror 83 and a corresponding side face of the semiconductor device 2. The focus position of the camera is adjusted according to the processes described in FIGS. 5 and 6.

FIG. 8 shows the situation that a rectangular semiconductor device 2 is inspected, wherein the semiconductor device 2 is rotated by 90° compared with the situation shown in FIG. 7. The second motor 14 carries out a symmetric position change of the second mirror 82 and the fourth mirror 84. By the position change a second distance 22 between second mirror 82 and a corresponding side face of the semiconductor device 2, as well as a second distance 22 between fourth mirror 84 and a corresponding side face of the semiconductor device 2 can be made equal to a first distance 21 between first mirror 81 and a corresponding side face of the semiconductor device 2, as well as equal to a first distance 21 between a third mirror 83 and a corresponding side face of the semiconductor device 2.

Figure 9:
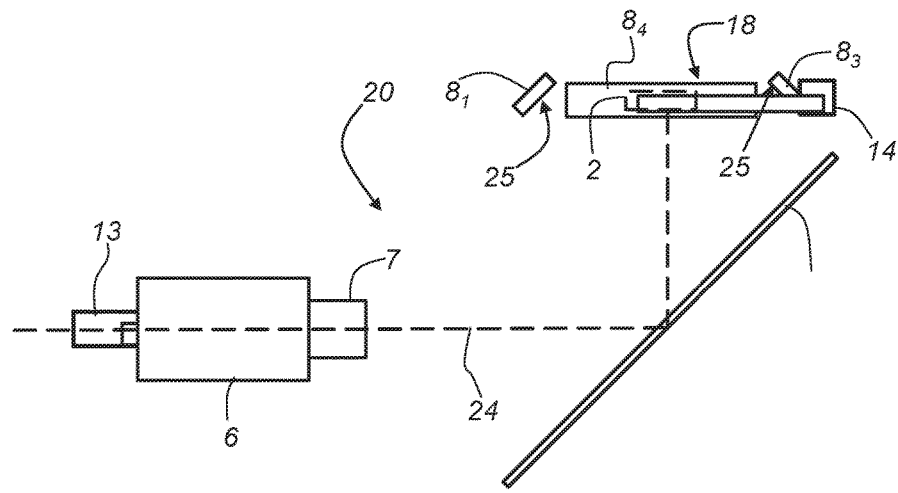
FIG. 9 is a schematic side view of the apparatus for carrying out the inspection of four side faces of a semiconductor device as shown in FIG. 5.

FIG. 9 is a is a schematic side view of the inventive apparatus 20 for carrying out the inspection of at least four side faces 31, 32, 33 and 34 of a semiconductor device 2 as shown in FIG. 5. The mirror block 18, having the first mirror 81, the second mirror 82, the third mirror 83, and the fourth mirror 84, surrounds the semiconductor device 2 for inspection. Each of the four mirrors 81, 82, 83 and 84 has a mirror surface 25 which is tilted by 40 to 48 degrees with respect to the side faces 31, 32, 33 and 34 of the semiconductor device 2. An image of the side faces 31, 32, 33 and 34 is reflected down to a tilted mirror 27. The tilted mirror 27 directs to the image of the side faces 31, 32, 33 and 34 from the mirror block 18 along the image beam path 24 to the camera 6.

Figure 10:
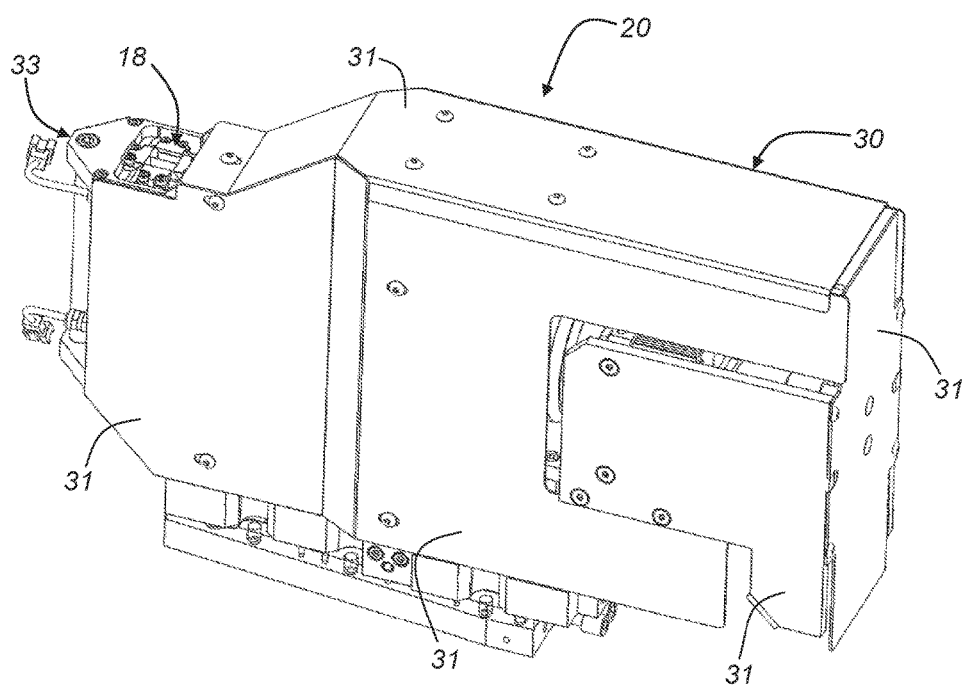
FIG. 10 is a perspective view of an embodiment of the inventive apparatus for the inspection of side faces of semiconductor devices.

FIG. 10 is a perspective view of an embodiment of the inventive apparatus 20 for the inspection of side faces of semiconductor devices 2 (not shown here). There are several wall panels 31 which together define a housing 30 of the apparatus 20. The housing 30 surrounds at least the camera 6 and the mirror block 18. The mirror block 18 is arranged at a first end 33 of the housing 30. As mentioned above, the mirror block 18 carries the first mirror 81, the second mirror 82, the third mirror 83, and the fourth mirror 84 (see FIGS. 5 to 8). The mirror block 18 defines the free space 16 (see FIG. 5) which is accessible from the outside the housing 30.

Figure 11:
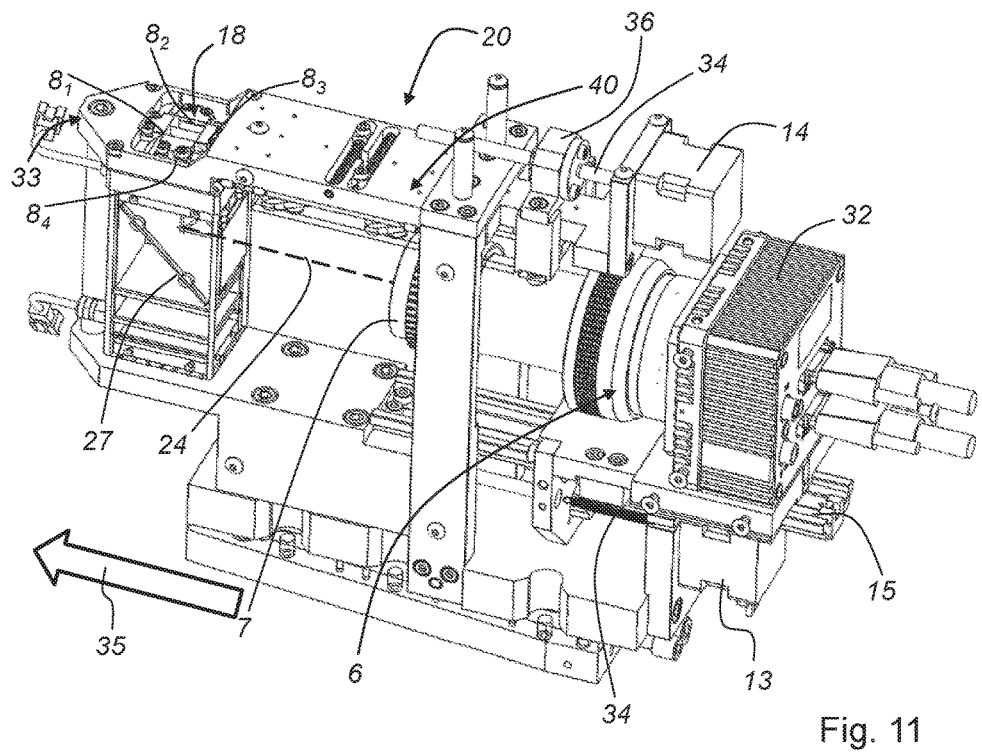
FIG. 11 is a perspective view of the embodiment of the inventive apparatus for the inspection of side faces of semiconductor devices as shown in FIG. 10, wherein housing parts are removed.

FIG. 11 is a perspective view of the inventive apparatus 20 for the inspection of side faces of semiconductor devices, wherein the wall panels 31 of the housing 30 have been removed. The apparatus 20 has a frame construction 40 which carries the camera 6 with the lens 7 and an electronic back 32; the mirror block 18, a tilted mirror 27 and at least one illumination device (see FIG. 13). According to the embodiment as described in FIGS. 10 to 13, the apparatus 20 forms a single module. Once this optical module is installed, a whole range of semiconductor device sizes (square and rectangular) can be handled without the need to install new parts. The module allows easy motorization. The first motor 13 is assigned to the camera 6 for an adjustment of a focus position of the camera 6. The second motor 14 is assigned to the opposing second mirror 82 and fourth mirror 84 (see FIGS. 5 to 8) for adjusting their position with respect to the semiconductor device. The first motor 13 and the second motor 14 are not coupled.

The first motor 13 can be part of the camera 6 with a zoom-lens 7 set-up with auto-focus as well. For the adjustment of the focus of the camera 6 the first motor 13 is coupled to a slide 15 by a leadscrew in order to carry out a linear movement 35 of the camera 6 and/or the lens 7 along the imaging beam path 24.

The second motor 14 drives a leadscrew 34, and via a cam mechanism 36 the second mirror 82 and the fourth mirror 84 are moved simultaneously.

The tilted mirror 27 directs an image of the mirror block 18 along the image beam path to the camera 6.

Figure 12:
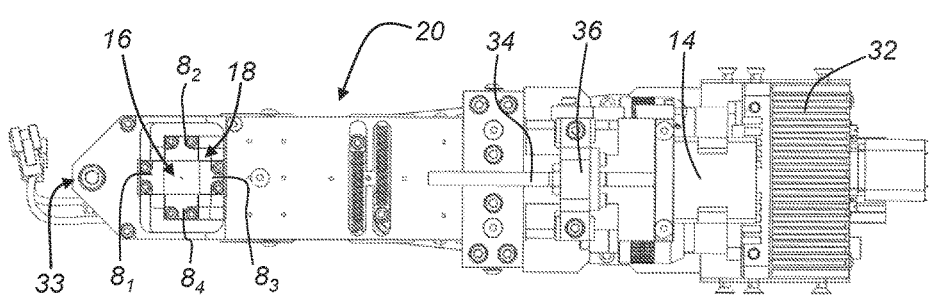
FIG. 12 is a top view of the embodiment of the inventive apparatus for the inspection of side faces of semiconductor devices as shown in FIG. 10, wherein housing parts are removed.

FIG. 12 is a top view of the inventive apparatus 20 for the inspection of side faces of semiconductor devices. As already mentioned in the description of FIG. 11 the housing parts have been removed. The free space 16 of the mirror block 18 can accommodate a whole range of semiconductor device sizes to be inspected, without the need of new parts. The whole apparatus 20 has a compact and elongated design. The apparatus 20 stretches from the first end 33 to the electronic back 32 of the camera. The first motor 13 and the second motor 14 fit into the compact and elongated design as well.

Figure 13:
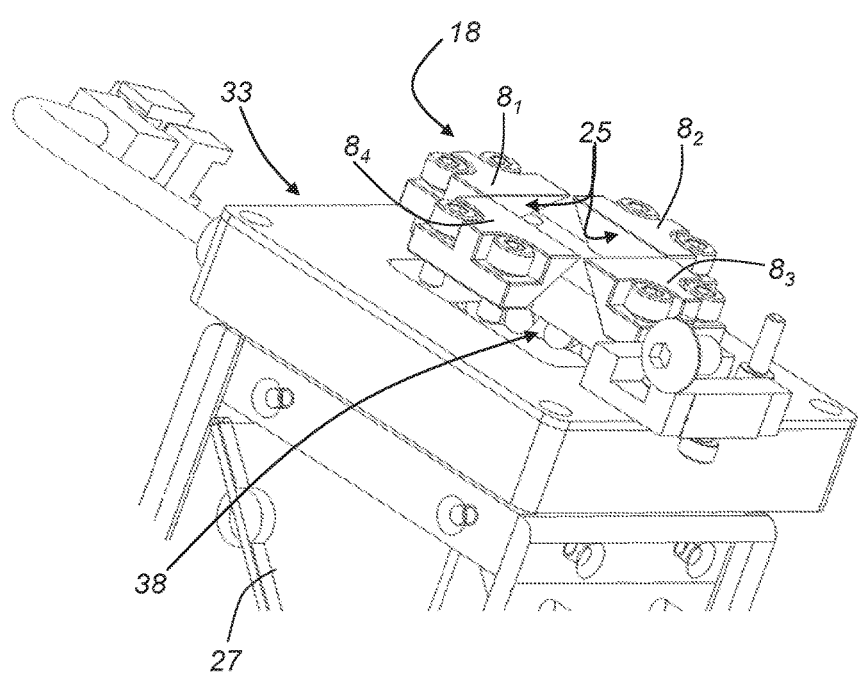
FIG. 13 is an enlarged perspective view of the mirror block of the embodiments shown in FIG. 10, 11 or 12; and, FIG. 14 is a schematic view of the turret for feeding semiconductor substrates to the mirror block.

FIG. 13 is an enlarged perspective view of the mirror block 18 at the first end 33 of the embodiments shown in FIGS. 10 and 11. Each of the first mirror 81, the second mirror 82, the third mirror 83, and the fourth mirror 84 has the mirror surface 25 tilted by 40 to 48 degrees. Under the mirror block 18 an illumination device is provided, in order to illuminate the semiconductor device which is positioned for inspection in the free space 16 defined by the first mirror 81, the second mirror 82, the third mirror 83, and the fourth mirror 84 of the mirror block 18. The images of the side faces of the semiconductor device are reflected by the tilted mirror 27 to the camera. Although not shown in the embodiment described above, one could also use a view of the bottom face of the semiconductor device, which allows bottom face inspection. In order to carry out the so called five sided-inspection (5S-inspection), a very large depth-of-focus is required, in order to keep both the side faces and the bottom face in focus.

Figure 14:
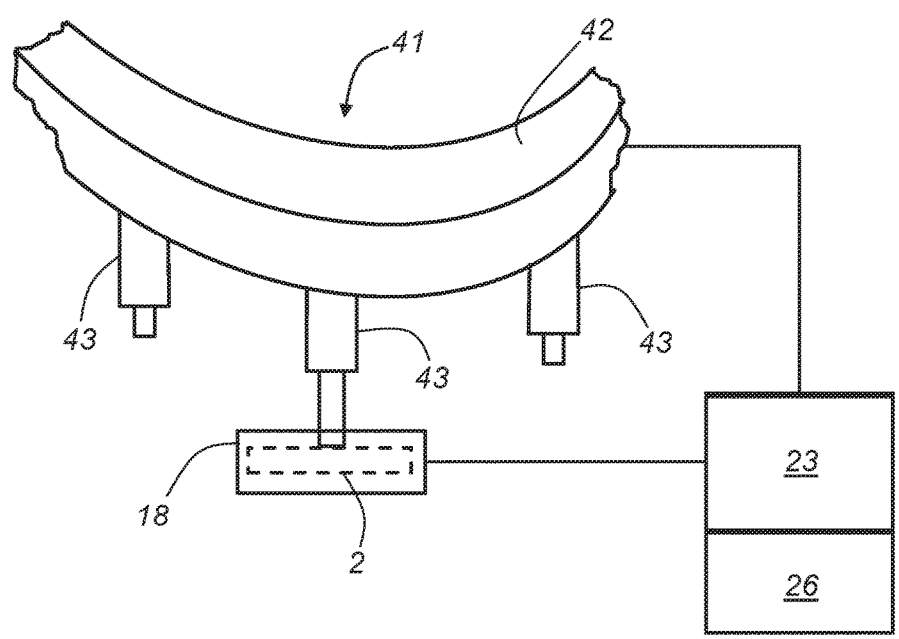

Due to the compactness of the apparatus 20 (see FIG. 10) the whole assembly can be mounted in a single slot of turret based machine 41. FIG. 14 is a schematic view of a turret 42 of the turret based machine 41 for feeding semiconductor substrates 2 to the mirror block 18. The turret 42 has a plurality of holding arms 43. By a control 23 the turret 42 is rotated in order to position the holding arms 43 with respect to the mirror block 18. Each holding arm 43 is configured to place the semiconductor device in the free space of the mirror block 18. Images from at least the four side faces are sent to a computer 26 for data processing. With the turret 42 a series of semiconductor devices 2 can be positioned automatically in the mirror block 18 for inspection.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

LIST OF REFERENCE NUMERALS 2 semiconductor device
31 first side face
32 second side face
33 third side face
34 fourth side face
4 top face
5 bottom face
6 camera
7 lens
81 first mirror
82 second mirror
83 third mirror
84 fourth mirror
9 defect, interior defect
10 image
11 optical length
12 optical length
13 first motor
14 second motor
15 slide
16 free space
17 rectangle
18 mirror block
20 apparatus
21 first distance
22 second distance
23 control
24 imaging beam path
25 mirror surface
26 computer
27 tilted mirror
30 housing
31 wall panels
32 electronic back
33 first end
34 leadscrew
35 linear movement
36 cam mechanism
38 illumination device
40 frame construction
41 turret based machine
42 turret
43 holding arm

What is claimed is:

1. An apparatus for inspecting at least side faces of a semiconductor device comprising:
   a camera, defining an imaging beam path;
   a mirror block, having a first mirror, a second mirror, a third mirror, and a fourth mirror, the mirrors being arranged such that they surround a free space in the form of a rectangle, and the opposing first mirror and third mirror are fixedly mounted and the opposing second mirror and fourth mirror are movably mounted; and
   a tilted mirror, for directing an image of at least the side faces semiconductor device from the mirror block to the camera.

2. The apparatus as claimed in claim 1, wherein a first motor is attached to the camera for an adjustment of a focus position of the camera.

3. The apparatus as claimed in claim 2, wherein the first motor is part of the camera with a zoom-lens set-up with auto-focus.

4. The apparatus as claimed in claim 2, wherein for the adjustment of the focus position of the camera, the first motor is configured to carry out a linear movement of the camera along the imaging beam path.

5. The apparatus as claimed in claim 4, wherein a leadscrew is driven by the first motor and the driven leadscrew is coupled to a slide of the camera.

6. The apparatus as claimed in claim 1, wherein a second motor is assigned to the opposing second mirror and fourth mirror for positioning the second mirror and the fourth mirror so that a first distance between a side face of the semiconductor device and the respective first and third fixed mirrors equals a second distance between a side face of the semiconductor device and the respective second and fourth mirrors.

7. The apparatus as claimed in claim 6, wherein a leadscrew is driven by the second motor and via a cam mechanism, the second mirror and the fourth mirror are moved simultaneously.

8. The apparatus as claimed in claim 1, wherein the first mirror, the second mirror, the third mirror, and the fourth mirror of the mirror block define a mirror surface which is tilted by 40 to 48 degrees.

9. The apparatus as claimed in claim 1, wherein an illumination device is provided to illuminate the semiconductor device which is positioned for inspection in the free space defined by the first mirror, the second mirror, the third mirror, and the fourth mirror of the mirror block.

10. The apparatus as claimed in claim 1, further comprising a turret having a plurality of holding arms, each holding arm configured to hold a semiconductor device to be inspected, and each holding arm in the plurality of holding arms is further configured to place the semiconductor device in the free space of the mirror block of the apparatus.

11. The apparatus as claimed in claim 1, wherein the camera, the mirror block, the tilted mirror, and an illumination device are arranged in a single module.

12. A method for inspecting at least side faces of a semiconductor device, the method comprising:
placing the semiconductor device centrally into a free space defined by a mirror block, the mirror block having a fixed first mirror, a fixed third mirror, a movable second mirror, and a movable fourth mirror;
providing information about a type of the semiconductor device to a control unit;
moving the second mirror and the fourth mirror such that a second distance between a respective side face of the semiconductor device and the second mirror and the fourth mirror is made equal to a first distance between a respective side face of the semiconductor device and the first mirror and the third mirror; and
adjusting a focus position of the camera along an imaging beam path to compensate for a change in a focal distance.

13. The method of claim 12, wherein a first motor adjusts the focus position of the camera by moving a zoom-lens set-up with auto-focus of the camera.

14. The method of claim 12, wherein a first motor adjusts the focus position of the camera by driving a leadscrew, and the leadscrew is coupled to a slide of the camera, for a linear movement of the camera.

15. The method of claim 12, wherein a second motor drives a leadscrew which acts on a cam mechanism for simultaneously moving the second mirror and the fourth mirror.

16. The method of claim 12, further comprising:
directing an image of the at least side faces of the semiconductor device via a tilted mirror into the imaging beam path of the camera; and
adjusting the focus of the camera.

17. The method of claim 16, wherein the tilted mirror directs in addition to the image of the at least side faces of the semiconductor device, an image of a bottom face of the semiconductor device into the imaging beam path of the camera, wherein the camera has a depth-of-focus so that the at least side faces and a bottom surface of the semiconductor device are kept in focus.

18. The method of claim 12, further comprising:
inserting the semiconductor device with a holding arm of a turret into the free space of the mirror block;
holding the semiconductor device during measurement in the free space of the mirror block; and
removing the semiconductor device with the holding arm of the turret from the free space of the mirror block.

19. A method for inspection of at least side faces of a semiconductor device, the method comprising:
rotating a turret with a plurality of holding arms, wherein each holding arm holds a single semiconductor device;
placing the respective semiconductor device with the respective holding arm centrally into a free space defined by a mirror block, having a fixed first mirror, a fixed third mirror, a movable second mirror, and a movable fourth mirror;
providing information about a type of the semiconductor device to a control unit;
moving the second mirror and the fourth mirror such that a second distance between a respective side face of the semiconductor device and the second mirror and the fourth mirror is equal to a first distance between a respective side face of the semiconductor device and the first mirror and the third mirror;
moving a camera along an imaging beam path to compensate for a change in a focal distance; and
removing the semiconductor device with the holding arm of the turret from the free space of the mirror block.

20. The method of claim 19, further comprising:
controlling a first motor and a second motor independently of each other, wherein the first motor moves the camera on a slide linearly in the direction of the imaging beam path, and wherein the second motor simultaneously moves the second mirror and the fourth mirror.

21. An apparatus for inspection of at least side faces of a semiconductor device comprising:
a housing, a camera, defining an imaging beam path and being linearly movable along the imaging beam path inside the housing;
a mirror block arranged at a first end of the housing, wherein the mirror block carries a first mirror, a second mirror, a third mirror, and a fourth mirror, the mirrors are arranged such that they surround a free space in the form of a rectangle and the free space is accessible from the outside of the housing, and wherein the opposing first mirror and third mirror are fixedly mounted and the opposing second mirror and fourth mirror are movably mounted; and
a tilted mirror arranged in the housing with respect to the camera and the mirror block, such that an image of at least the side faces of the semiconductor device in the mirror block is directed to the camera.

22. The apparatus as claimed in claim 21, wherein a first motor is arranged in the housing and assigned to the camera.

23. The apparatus as claimed in claim 21, wherein a second motor is arranged in the housing and assigned to the opposing second mirror and fourth mirror for positioning the second mirror and the fourth mirror so that a first distance between a side face of the semiconductor device and the respective first and third mirrors equals a second distance between a side face of the semiconductor device and the respective second and fourth mirrors.

24. A computer program product disposed on a non-transitory computer readable medium for inspection of at least side faces of a semiconductor device, the product comprising computer executable process steps operable to control a computer to:
place the semiconductor device with a placing mechanism into a free space of a mirror block;
determine a type to the semiconductor device;
move, according to the type to the semiconductor device, a second mirror and a fourth mirror of the mirror block such that a second distance between a respective side face of the semiconductor device and the second mirror and the fourth mirror is made equal to a first distance between a respective side face of the semiconductor device and a first fixed mirror and a third fixed mirror of the mirror block; and
adjusting a focus position of a camera along an imaging beam path in order to obtain a focused image of the at least side faces of the semiconductor device.

* * * * *